(12) United States Patent
Dai et al.

(10) Patent No.: US 11,752,364 B2
(45) Date of Patent: Sep. 12, 2023

(54) CABIN TYPE BEAM IRRADIATION APPARATUS AND BEAM IRRADIATION METHOD

(71) Applicants: Jianrong Dai, Beijing (CN); Chuanmeng Niu, Beijing (CN)

(72) Inventors: Jianrong Dai, Beijing (CN); Chuanmeng Niu, Beijing (CN)

(*) Notice: Subject to any disclaimer, the term of this patent is extended or adjusted under 35 U.S.C. 154(b) by 267 days.

(21) Appl. No.: 17/225,363

(22) Filed: Apr. 8, 2021

(65) Prior Publication Data

US 2021/0316160 A1 Oct. 14, 2021

(30) Foreign Application Priority Data

Apr. 9, 2020 (CN) .......................... 202010276953.6

(51) Int. Cl.
*A61N 5/00* (2006.01)
*A61N 5/10* (2006.01)

(52) U.S. Cl.
CPC ......... *A61N 5/1081* (2013.01); *A61N 5/1039* (2013.01); *A61N 5/1042* (2013.01); *A61N 5/1049* (2013.01); *A61N 2005/105* (2013.01); *A61N 2005/1094* (2013.01)

(58) Field of Classification Search
None
See application file for complete search history.

(56) References Cited

U.S. PATENT DOCUMENTS

| 5,851,182 | A | * | 12/1998 | Sahadevan | A61N 5/1049 378/65 |
| 8,664,618 | B2 | * | 3/2014 | Yao | A61N 5/1082 378/65 |
| 2001/0007588 | A1 | * | 7/2001 | Iizuka | A61B 6/504 378/209 |
| 2005/0236588 | A1 | * | 10/2005 | Ein-Gal | A61N 5/10 250/515.1 |
| 2012/0006363 | A1 | * | 1/2012 | Milojevic | B08B 3/024 134/144 |

* cited by examiner

*Primary Examiner* — Hoon K Song
(74) *Attorney, Agent, or Firm* — Chang & Hale LLP

(57) ABSTRACT

A cabin type beam irradiation apparatus and a method for performing beam irradiation method are provided. According to an embodiment, the beam irradiation apparatus comprises: a gantry having a hollow frame structure, the hollow portion of which being formed as a treatment cabin; a first guide rail, which is fixedly arranged on the frame; a treatment head, which is slidably arranged on the first guide rail; and an entry door, which may be openably and closably arranged on the gantry. The beam irradiation apparatus can perform radiotherapy on patients in a standing or sitting posture. Imaging guidance is additionally used to ensure the accuracy of the treatment position, and thus highly focused radiation is achieved by (non)coplanar radiotherapy. Further, the apparatus may have self-shielding function, and can reduce the difficulty and cost for construction of a machine room.

12 Claims, 6 Drawing Sheets

CABIN TYPE BEAM IRRADIATION APPARATUS AND BEAM IRRADIATION METHOD

CROSS-REFERENCE TO RELATED APPLICATIONS

The present application claims the benefit of, and priority to, a Chinese patent application No. 202010276953.6, entitled "CABIN TYPE BEAM IRRADIATION APPARATUS AND BEAM IRRADIATION METHOD", filed on Apr. 9, 2020, the disclosure of which is hereby expressly incorporated by reference herein in its entirety.

TECHNICAL FIELD OF THE DISCLOSURE

The present application generally relates to the field of radiotherapy equipment, and in particular, to a cabin type beam irradiation apparatus and beam irradiation method.

BACKGROUND

As one of the important methods for tumor treatments, radiotherapy occupies an important position in the field of tumor treatments. According to estimates, radiotherapy is necessary for 60 to 70% of all the malignant tumor patients. During radiotherapy, a patient needs to be accurately positioned to ensure that the part of the body to be irradiated, especially the tumor target area, receives a sufficiently high radiation dose, meanwhile minimizing damages to the healthy tissues of the patient.

More than 90% of the existing radiotherapy is carried out based on the C-arm radiotherapy machine, that is, a C-shaped arm is used to drive the treatment head to rotate around the lying patient in the range of 0-360° to achieve dose delivery. During conventional coplanar irradiation, the treatment couch angle is zero degree, and all the central axes of the radiation field are located in the same plane. The beam arrangement is relatively simple, but the selection range of beam angles is limited, which is detrimental to the protection of organs at risk. Ideally, non-coplanar radiotherapy can expand the selection range of beam angles to the entire three-dimensional space, which is more beneficial to the protection of organs at risk and the increase of prescription doses, thereby further improving the local tumor control rate. However, the non-coplanar radiotherapy based on the C-arm linear accelerator (C-Linac) needs to be realized in conjunction with the rotating of treatment couch. Due to the collision between the gantry and the treatment couch or the patient body, most of the non-coplanar angles cannot be implemented; and during treatment, each non-coplanar beam requires a technician to enter the treatment room to manually turn the couch to a corresponding angle, which will result in positioning errors and increase the treatment time significantly. Therefore, the clinical application of non-coplanar radiotherapy technique based on the C-Linac is rare.

Researchers have designed a variety of non-coplanar radiotherapy devices. For example, a Chinese patent (application number 201110447735.5) discloses a 4D stereotactic radiotherapy device that allows the beam irradiation head to follow the gantry to nod or head up to achieve the adjustment of the beam angle in the three-dimensional space and contributes to the accurate detection and non-coplanar treatment. A Chinese patent (application number 201410558872.X) discloses a five-degree-of-freedom O-arm radiotherapy system, which realizes the five-degree-of-freedom controlled radiotherapy process with high control accuracy and stability, and improves the feasibility of non-coplanar radiotherapy. Another Chinese patent (application number 201810078431.8) discloses a cage type radiotherapy device, which can achieve rapid and accurate non-coplanar treatment with a large stereo angle range without moving the patient, through a multi-degree-of-freedom movement of a radiation beam generating mechanism. However, the radiotherapy devices disclosed in the above mentioned patents have complicated structures, which is not conducive to the realization of the devices; the main beam area is large, thus the shielding requirements for the treatment room are relatively high, which increases the difficulty of the design and construction of the treatment room.

SUMMARY

In order to overcome the shortcomings of the prior art, one aspect of the present application proposes a cabin type beam irradiation apparatus, which can implement non-coplanar radiotherapy. By combining the movement of both the treatment head and the patient body, non-coplanar radiation in a wide range of angles can be realized, and the area of the main beam of the treatment head is greatly reduced, which facilitates the self-shielding design to reduce the difficulty of building a radiotherapy machine room.

According to an exemplary embodiment of the present application, there is provided a cabin type beam irradiation apparatus, comprising: a gantry having a hollow frame structure, the hollow portion of the frame structure being formed as a treatment cabin; a first guide rail, which is fixedly arranged on the gantry; a treatment head, which is slidably arranged on the first guide rail; and an entry door, which is openably and closably arranged on the gantry.

In some embodiments, a rotating shaft is installed at one end of the entry door, and a mounting hole is formed on an upper part of the gantry, and the rotating shaft forms a revolute pair with the mounting hole, such that the entry door can be opened and closed relative to the gantry. In a specific embodiment, rotating shafts may be provided on opposite sides of one end of the entry door, and correspondingly, two mounting holes are provided on the upper part of the gantry, which can improve the stability of the entry door.

In some embodiments, a skylight is installed on a top of the gantry, and a window of lead glass for daylighting and a ventilation window are arranged around the skylight. In a specific embodiment, the skylight has a hollow structure and is arranged on the top of the gantry, so that the head of the patient will not collide with the gantry while the patient body is lifted.

In some embodiments, the radiotherapy apparatus further comprises: a second guide rail fixedly arranged on the entry door and arranged opposite to the first guide rail; and a radiation detector slidably arranged on the second guide rail and configured to face the treatment head directly during beam irradiation treatment.

In some embodiments, the radiotherapy apparatus further comprises: an imaging assembly fixedly arranged on the hollow frame structure of the gantry.

In some embodiments, the imaging assembly comprises one or more groups of cone beam imaging units; in another embodiment, the imaging assembly comprises one or more groups of fan beam imaging units or magnetic resonance imaging units. In a specific embodiment, the imaging assembly may comprise two magnets facing each other or two groups of coils facing each other for generating a magnetic field.

In some embodiments, the radiotherapy apparatus further comprises: a shielding plate arranged on the gantry and/or the entry door, so as to shield or greatly reduce the leakage of beam and reduce the radiation dose outside the treatment cabin. In a specific embodiment, the shielding plate may comprise a side shielding plate and/or a main shielding plate and/or a rear shielding plate, wherein the side shielding plate is installed on a side of the gantry, and the main shielding plate is installed on an outer surface of the entry door, and the rear shield plate is installed on a rear side of the gantry directly opposite to the main shielding plate.

In some embodiments, the first guide rail is an arc-shaped guide rail, and the treatment head comprises a radiation source, a collimator, and a treatment head frame, wherein the collimator is fixedly mounted below the radiation source, the radiation source is fixedly installed on the treatment head frame, and two opposite sides of the treatment head frame are provided with an arc-shaped chute that can slide on the first guide rail.

In other embodiments, the first guide rail is a linear guide rail, and the treatment head comprises a radiation source, a collimator, a treatment head frame, and a sliding frame, wherein the collimator is fixedly installed below the radiation source, the radiation source is fixedly installed on the treatment head frame, the treatment head frame is rotatably installed on the sliding frame, and two opposite sides of the sliding frame are provided with a chute that can slide on the first guide rail.

In some embodiments, the radiotherapy apparatus further comprises: a base, on which the gantry is fixedly mounted; a third guide rail, which is provided on the base and extends into the hollow portion of the gantry; and a human body supporting structure, which is slidably arranged on the third guide rail. In a specific embodiment, the third guide rail is a linear guide rail for guiding the human body supporting structure to move from an initial positioning position to a treatment position, and for guiding the human body supporting structure to return to the initial positioning position after the treatment.

In some embodiments, the human body supporting structure comprises a supporting base and a supporting frame, wherein the supporting base is slidably disposed on the third guide rail, and the supporting frame is disposed on the supporting base, which can drive the supporting frame to move with multiple degrees of freedom.

In some embodiments, the radiotherapy apparatus further comprises: a stopper, which is arranged on the base. The stopper comprises a first stopper and a second stopper, wherein the first stopper is installed at one end of the base and is used to define the initial position of the human body supporting structure while the second stopper is installed at the other end of the base and is used to define the treatment position of the human body supporting structure.

According to another aspect of the present application, there is provided a beam irradiation method for radiotherapy, which comprises: (1) using a positioning body cover to fix a patient in standing or sitting posture on a human body supporting structure of a radiotherapy apparatus to perform an initial positioning; (2) opening an entry door of the radiotherapy apparatus, and guiding the human body supporting structure to an imaging position, which is located in the enclosed space of the radiotherapy apparatus; (3) closing the entry door, imaging a target area of the patient by using an imaging assembly of the radiotherapy apparatus to obtain an positioning error, and correcting the positioning error; or modifying an irradiation plan based on an evaluation of the positioning error and a change in anatomical structure obtained through the imaging; and (4) performing beam irradiation on the patient body according to a treatment plan, wherein, during the irradiation process, the imaging assembly performs real-time imaging of the target area, and monitors the position and morphology of the target area to realize controlled or real-time tracking irradiation.

In some embodiments, the positioning body cover used in the step (1) is made of a thermoplastic film, vacuum pad, strap or styrofoam for a human body in standing or sitting posture. For imaging positioning, a marking point is provided on the positioning body cover, and three positioning laser lights orthogonal to each other are used to assist in achieving the relative fixation between the patient and the human body supporting structure. The initial positioning is performed through the movement of the human body supporting structure until the marking point on the positioning body cover coincides with the marking lines of the three positioning laser lights.

In some embodiments, in the step (2), the human body supporting structure slides along a guide rail to the imaging position, at which the human body supporting structure base abuts against a stopper.

In some embodiments, in the step (3), the imaging is performed through cone beam imaging, fan beam imaging, or magnetic resonance imaging. In a specific embodiment, when cone beam imaging is used, a cone beam imaging assembly is used to obtain a plurality of perspective images of the patient while the human body supporting structure drives the patient to rotate, and reconstruct a three-dimensional image. When fan beam imaging is used, a fan beam imaging assembly is used to perform axial scan or spiral scan imaging while the human body supporting structure drives the patient to lift and lower and rotate. When magnetic resonance imaging is used, the patient body remains fixed.

In some embodiments, in the step (4), during real-time imaging monitoring of the target area performed by the imaging assembly, when one group of cone beam imaging assembly is used, the position and morphology of the target area can be monitored in connection with an orthogonal and perspective image obtained by a radiation detector. When two groups of orthogonal cone beam imaging assemblies or fan beam imaging assemblies are used, the position and morphology of the target area can be monitored through orthogonal and perspective images of the target area obtained in real time by the two groups of imaging assemblies. When magnetic resonance imaging is used, the position and morphology of the target area are monitored by obtaining a tomographic image of the target area in real time.

The radiotherapy apparatus of the present application has a simple structure and can be used to perform radiotherapy on patients in standing or sitting posture. The device has an imaging guidance function, through which high-precision coplanar or non-coplanar radiotherapy can be realized. In addition, the safety of non-coplanar radiotherapy is high, and there is no risk of collision between the treatment head and the patient body, which is beneficial for the realization of highly automated and efficient non-coplanar radiotherapy. In addition, the radiotherapy device of the present application has self-shielding function, thereby the difficulty and cost of machine room construction can be reduced.

The above description describes certain aspects, advantages, and novel features of the present application for the purpose of summarizing the present application. It should be understood that according to any particular embodiment of the present application, it is not necessary to achieve all these advantages. Therefore, the present application can be embodied or implemented in a manner that one advantage or one group of advantages taught herein are achieved or optimized, without having to achieve other advantages taught or disclosed herein.

BRIEF DESCRIPTION OF THE DRAWINGS

Various aspects of at least one example are discussed below with reference to the accompanying drawings, which are not intended to be drawn to scale. The drawings are included to provide an explanation and further understanding of various aspects and examples, and are incorporated in and constitute a part of this specification, but are not intended to serve as a definition of the limits of this application. In the drawings, each identical or nearly identical component shown in each figure is represented by the same numeral. For the sake of clarity, not every component is labeled in every drawing. In the picture.

DETAILED DESCRIPTION

In order to make it easy to understand the technical means, creative features, objectives and effects achieved by the present application, the technical solutions in the embodiments of the present application will be clearly and completely described below in conjunction with the accompanying drawings. Obviously, the described embodiments are only a part of the embodiments of the present application, and the present application is not limited to the precise form of these exemplary embodiments.

Figure 1:
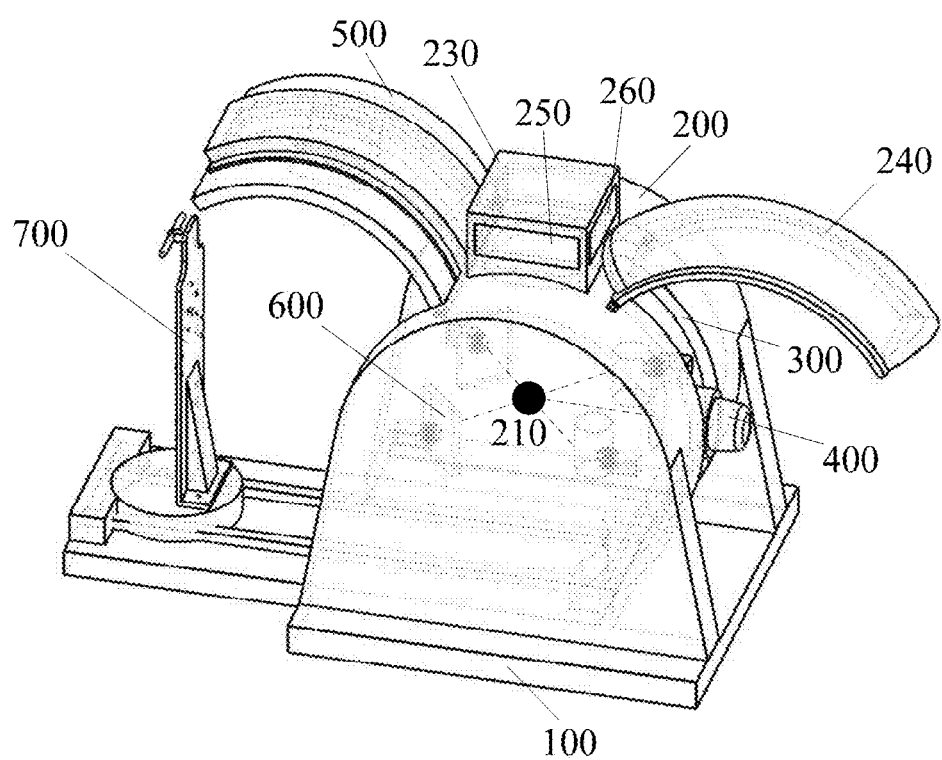
FIG. 1 is a perspective view of a beam irradiation apparatus according to an embodiment of the present application.

FIG. 1 shows a three-dimensional structural diagram of a cabin type beam irradiation apparatus according to an embodiment of the present application. As shown in FIG. 1, the cabin type beam irradiation apparatus of the embodiment of the present application comprises: a base 100 for supporting other parts of the treatment device; a gantry 200 fixed on the base 100 and having a hollow frame structure, wherein the hollow portion of the frame structure is formed as a treatment cabin; a first guide rail 300 fixedly arranged on the gantry 200; a treatment head 400 slidably arranged on the first guide rail 300; and an entry door 500, which is openably and closably mounted on the gantry 200. It can be appreciated that the beam irradiation apparatus may not comprise the base 100; in this case, the gantry is directly set on the ground of a machine room.

In the embodiment shown in FIG. 1, the gantry 200 has generally a cylindrical cabin structure, two ends of which are supported and fixed by a cradle, and the patient can enter the cabin through the entry door to receive radiotherapy. The first guide rail 300 and the entry door 500 are oppositely arranged on both sides of the gantry 200. The first guide rail 300 is suitable for position adjustment of the treatment head, and has substantially a same contour as a side surface of the gantry, for example, an arc-shaped structure. The first guide rail can be fastened to the gantry by means of bolts or the like. In some embodiments, the first guide rail can also be integrally formed as a part of the frame. In order to stably support the treatment head 400, the first guide rail 300 may comprise a pair of opposite guide rails located on both sides of the treatment head 400. Accordingly, corresponding chutes can be provided on both sides of the beam treatment head 400, thus the treatment head can slide on the guide rail to adjust the position and angle of the beam according to clinical requirements, so that the central axis of the beam is aligned with a treatment center 210.

The entry door 500 may also have substantially a same contour as the side surface of the gantry 200, for example, an arc-shaped structure. When the entry door is closed, it can abut against the gantry 200 to close the treatment cabin. A rotating shaft (not shown) may be installed at one end of the entry door 500, a mounting hole is formed on the upper part of the gantry 200, and the rotating shaft forms a revolute pair with the mounting hole, so that the entry door 500 can be operated to open and close the treatment cabin. In a specific example, a pair of mounting holes for installing the entry door are provided on opposite sides of the top of the gantry 200, and both sides of the upper end of the entry door are provided with rotating shafts to form revolute pairs with the mounting holes on the upper part of the gantry, so that the entry door can be opened and closed relative to the gantry. The entry door 500 can be opened manually; alternatively, the entry door can also be opened and closed in an electrically controlled manner by connecting the rotating shaft with electromechanical devices such as motors and actuators. The entry door opens upwards to facilitate patients to enter into the treatment cabin. The entry door abuts against closely the frame of the gantry to close the treatment cabin when it moves downwards.

In one embodiment, as shown in FIG. 1, a skylight 230 is provided on the top of the gantry 200. The skylight 230 can be formed directly above the treatment center 210 and has a hollow structure which communicates with the hollow portion of the gantry 200 so that the head of patients would not collide with the frame when the human body is raised and lowered. In a specific example, lead glass 260 is provided on at least one circumferential side of the skylight 230, which can be used for daylighting and shielding beams, and at least another circumferential side of the skylight is provided with a ventilation window 250 to improve air circulation in the treatment cabin. In a specific embodiment, the circumferential sides of the skylight 230 may be provided with two pieces of lead glass 260 arranged oppositely and two ventilation windows 250 arranged oppositely.

As shown in FIG. 1, the radiotherapy apparatus may further comprise an imaging assembly 600 and a human body supporting structure 700, the specific structure of which will be described in detail below.

Figure 2:
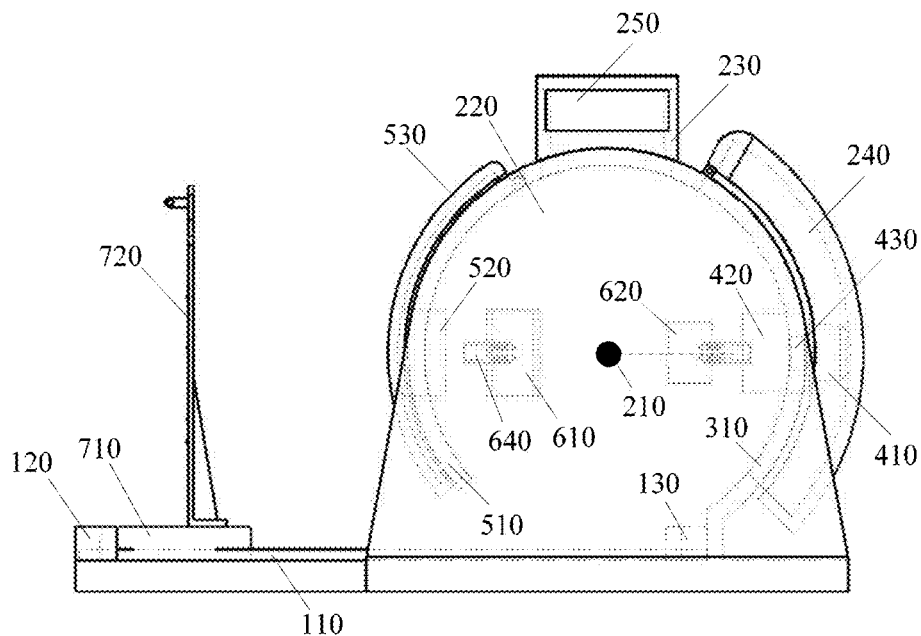
FIG. 2 is a front view of a beam irradiation apparatus according to an embodiment of the present application.

FIG. 2 shows a front view of a beam irradiation apparatus according to an embodiment of the present application, in which the entry door 500 is closed. As shown in FIG. 2, the cross section of the gantry 200 is generally circular, the first guide rail is an arc-shaped guide rail 310, which is installed on the gantry 200. The treatment head 400 can slide up and down along the first guide rail 310 to a certain angle, and the central axis of the beam generated by it can pass through the treatment center 210. During radiotherapy, the treatment center 210 generally coincides with the center of the tumor target area of patients.

As shown in FIG. 2, the cabin type beam irradiation apparatus further comprises a second guide rail 510 and a radiation detector 520. The second guide rail 510 is fixedly arranged on the entry door 500 and is arranged opposite to the first guide rail 300. The radiation detector 520 is slidably arranged on the second guide rail 510, which faces oppositely to the radiation beam treatment head 400 during treatment. Similar to the first guide rail 300, the second guide rail 510 also has substantially a same contour as the side surface of the gantry, for example, an arc-shaped structure. The radiation detector 520 can slide on the second guide rail 510 to adjust its position, and the radiation treatment head and the radiation detector are controlled to move synchronously by the means of an automatic control device during radiotherapy, so that the central axis of the radiation beam of the treatment head can always penetrate vertically the center of the radiation detector 520. The radiation detector 520 may be an MV-level detector, a kV-level detector, a radiation blocker, or the like.

The cabin type beam irradiation apparatus may further comprise an imaging assembly 600 for imaging the target area of the patient, which may be fixedly arranged on the hollow frame structure of the gantry 200.

In an exemplary embodiment, the imaging assembly 600 may be configured for X-ray imaging, which comprises at least one X-ray imaging unit, each of which may comprise a radiation source and an opposite detector. For example, fan beam or cone beam X-ray imaging can be used to perform computed tomography (CT). Four-dimensional CT imaging can be performed by monitoring the target area of the patient in real-time to simulate the positioning of the target area of the patient, verify the positioning of the patient body or monitor the positioning of the target area in real-time, so as to assist beam radiation.

In a specific embodiment, the imaging assembly may be a cone beam imaging (CBCT) system, which comprise one or more groups of cone beam imaging units, each group of which may comprise a cone beam tube 610 and a cone beam detection plate 620. The cone beam tube 610 and the cone beam detection plate 620 are installed at a middle height of the gantry 200 facing oppositely to each other by a supporting arm 640, for example, at a same height as the treatment center 210. If two groups of imaging units are used, as shown in FIGS. 1-2, the two cone beam x-ray tubes can be installed at the middle height of the gantry 200 at both sides of the first guide rail 300, and the two cone beam detection plates are installed directly opposite to the two cone beam x-ray tubes at the middle height of the gantry. The two groups of imaging units are arranged orthogonally to each other, that is, the central axes of the two cone beam tubes are perpendicular to each other in a plane at the middle height of the gantry. The two groups of imaging units can either perform CBCT imaging or be used for orthogonal and perspective imaging.

In another specific embodiment, the imaging assembly may also be a fan beam imaging (CT) system, which comprise one or more groups of fan beam imaging units, each group of which may comprise a fan beam tube and a fan beam detection plate, which are installed at the middle height of the frame facing oppositely to each other. If two groups of imaging units are used, the two fan beam tubes are installed at the middle height of the frame and are located at both sides of the first guide rail 300, and the two fan beam detection plates are installed on the opposite sides of the two fan beam tubes at the middle height of the gantry 200 respectively. The two groups of imaging units are arranged orthogonally to each other, that is, the central axes of the two fan beam tubes are perpendicular to each other in a plane at the middle height of the gantry. When performing fan beam imaging, the human body support structure drives the human body to lift and lower and rotate while the fan beam tube is emitting x-ray, so as to obtain spiral tomographic images.

Figure 3:
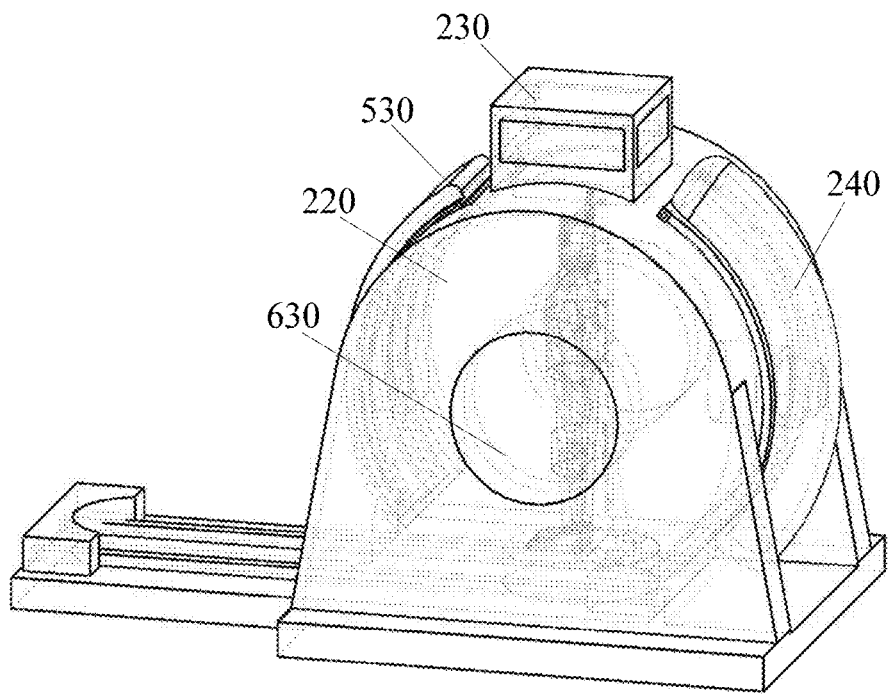
FIG. 3 is a perspective view of a beam irradiation apparatus according to another embodiment of the present application.

In order to achieve imaging of different parts of the patient, the imaging assembly of the present application can also use a magnetic resonance imaging unit for performing magnetic resonance imaging on the patient to achieve positioning simulation, positioning verification or real-time monitoring of the target area of the patient. As shown in FIG. 3, the imaging assembly 600 comprises two magnets 630 facing opposite to each other directly. The two magnets 630 can be arranged in parallel, and are arranged in a mounting hole on both sides of the gantry 200 respectively. The magnet may be a permanent magnet, such as a circular permanent magnetic plate, or a magnetic resonance coil. The distance between the two magnets allows the human body supporting structure to pass through. When using magnetic resonance imaging to perform positioning imaging of a patient, it is also necessary to install an excitation coil on the human body supporting structure aligning with the tumor target area. The magnetic coil can receive signals for MRI imaging.

As shown in FIG. 2, the beam irradiation apparatus may further comprise a shielding plate, which can prevent radiation leakage and improve the safety of the radiotherapy device. In an embodiment, the shielding plate may comprise a side shielding plate 220, a main shielding plate 530, and/or a rear shielding plate 240. Wherein, the side shielding plates 220 are installed on opposite sides of the gantry 200, which are heavy metal plates with a certain thickness and can realize the side sealing of the gantry 200 through shielding or greatly reducing the lateral leakage of beams. The main shielding plate 530 is installed on an outer surface side of the entry door 500 and it is also a heavy metal plate with a certain thickness. When the entry door is closed, the main shielding plate 530 can block the beam from leaking through the entry door 500. The rear shielding plate 240 is also made of metal material, and it is installed on the side of the gantry 200 directly opposite to the main shielding plate 530. The rear shielding plate 240 may have substantially the same contour as the side of the gantry so that it abuts against the gantry closely when closed. Referring to FIG. 1, similar to the entry door 500, the rear shielding plate 240 is provided on the gantry 200 in an openable and closable manner. At one end of the rear shielding plate 240 there is provided a rotating shaft, which forms a revolute pair with a mounting hole on the upper part of the gantry. The rear shielding plate 240 can also be provided with an arched inner cavity so that it will not collide with the treatment head 400 when closed.

Through the self-shielding design of the present application, the radiation can be constrained to the inside of the radiotherapy device to the greatest extent, and thus the radiation dose outside the treatment cabin is greatly reduced, thereby reducing the protection requirements on the design of the radiation machine room and the construction cost of the machine room. As shown in FIG. 2, when the entry door is closed, a lower end of the entry door 500 may not contact with the base 100 rather be spaced from the base to prevent the entry door from being worn out, or it may be designed to have a groove structure to match closely with the guide rails, to further prevent radiation leakage.

In order to control precisely the positioning of the patient, as shown in FIGS. 1-2, the beam irradiation apparatus of the present application preferably comprises a base 100, on which the gantry 200 can be fixedly installed. The width of the base 100 can be smaller than that of the gantry 200 but should be greater than the width of the entry door 500. A third guide rail 110 and a human body supporting structure 700 are also provided on the base 100. For example, the horizontal axis of the third guide rail 110 may coincide with the beam emitted by the beam irradiation treatment head on the horizontal plane, thereby improving the positioning accuracy and further improving the implementation efficiency of non-coplanar radiotherapy.

As shown in FIGS. 1-2, the third guide rail 110 is arranged on the base 100 and extends into the hollow portion of the gantry 200, which can be a group of linear guide rails for guiding the human body supporting structure 700 from the initial positioning position to the treatment position. The human body supporting structure 700 is slidably arranged on the third guide rail 110. At the initial position, the patient stands on the human body supporting structure 700 and completes the initial positioning. When preparing for radiotherapy, the entry door 500 is opened, and the human body supporting structure 700 is guided by the third guide rail 110 to the treatment position within the gantry 200. The human body supporting structure, on the one hand, can help fix the human body in a standing or sitting posture, and on the other hand, can drive the human body to carry out a multi-degree of freedom movement, such as lifting and lowering, translating, pitching, rolling and yawing. Through the lifting and lowering movement, the treatment head can be aimed right at the target area of the patient. Through the movement of translating, pitching, rolling, and yawing, the positioning error can be corrected. In addition, through the movement of yawing, the human body can be rotated around the vertical axis of a supporting base of the human body supporting device, thereby achieving multi-angle fixed field radiotherapy, or volumetric modulated arc therapy (VMAT).

The human body supporting structure 700 may comprise a supporting base 710 and a supporting frame 720, wherein the supporting base 710 is slidably disposed on the third guide rail 110, and the supporting frame 720 can be fixedly installed on the supporting base 710. The supporting base 710 can drive the supporting frame 720 to perform multi-degree-of-freedom movement, such as three-axis translation and rotation, to achieve imaging of the target area and positioning adjustment, so that the treatment head is aimed at the treatment target area during irradiation treatment. The supporting base 710 is slidable along the third guide rail 110. A power driving device is arranged inside the supporting base 710, so that it permits multi-degree-of-freedom movement, so as to drive the supporting frame 720 to achieve lifting and lowering, translation, and rotation movements to achieve patient positioning and correction of a positioning error. For example, the supporting base can be designed as a multi-layer structure, such as a three-layer structure. The lower structure platform enables the supporting base to drive the supporting frame to move up and down and can drive the supporting frame to move horizontally on the third guide rail. The middle structure platform enables the supporting base to drive the supporting frame to rotate, and the upper structure platform enables the supporting base to drive the supporting frame to move vertically. The supporting frame 720 may be a body plate erected on the supporting base. As shown in FIGS. 1-2, it is a substantially L-shaped plate. The lower part is installed on the supporting base through bolt connections, etc., and an armrest is installed on the upper part for a standing patients to grasp. The armrest may have a T shape or other shapes, and the height can be adjusted according to the height of the patients. The lower part of the body plate can be provided with ribs, rib plates and other reinforcements to improve the stability of the structure. A plurality of locking mesh holes can also be arranged on the upper part of the body plate to facilitate fixing a thermoplastic mesh on the body plate, which can be used to cover the treatment site of a patient when the head or neck tumor of the patient is subjected to radiotherapy. During treatment, the body of a patient in a standing or sitting posture can be firmly fixed to the supporting frame by using accessories such as a body cover made of a thermoplastic film, a vacuum pad, a strap, or a styrofoam.

In order to ensure the start-stop stability of the human body supporting structure, prevent the human body from shaking, and facilitate accurate positioning of the patient, the beam irradiation apparatus may further comprise a stopper arranged on the base. In an embodiment of the present application, the stopper may be provided at both ends of the third guide rail 110, wherein a first stopper 120 is installed at one end of the base 100 to limit the initial position of the human body supporting structure, and prevent the human body supporting structure from shaking when it reaches the initial position. A second stopper 130 is installed at the other end of the base 100 to limit the treatment position of the human support structure 700 and prevent the human support structure from shaking when it reaches the treatment position. The first stopper 120 should be positioned such that the entry door 500 does not collide with the supporting frame 720 during the opening, and its one end in contact with the supporting base 710 has an arc shape to match the shape of the supporting base 710 (as shown in the FIG. 3). One end of the second stopper 130 can be leaned against the lower part of the gantry 200, and the other end has an arc shape to match the shape of the supporting base 710. Preferably, the position and size of the second stopper are designed such that the supporting base 710 coincides with the treatment center or is located near the treatment center when it is in contact with the second stopper 130.

As shown in FIGS. 1-3, in an embodiment of the present application, the first guide rail 300 that supports the treatment head 400 and guides it to move is an arc-shaped guide rail, and the treatment head can move up and down on a vertical plane along the guide rail at a certain angle. When the treatment head slides along the guide rail, the central axis of the beam always passes through the treatment center 210. In this embodiment, as shown in FIG. 2, the treatment head comprises a radiation source 410, a collimator 420, and a treatment head frame 430. The radiation source 410 may be an x-ray source generated by a linear accelerator (such as MV level) or electron beam source, or gamma-ray source produced by radioactive materials. The collimator 420 is fixedly installed below the radiation source 410, and the radiation source 410 is fixedly installed on the treatment head frame 430. Both sides of the treatment head frame 430 are provided with arc-shaped chutes that can slide on the first guide rail 300.

Figure 4:
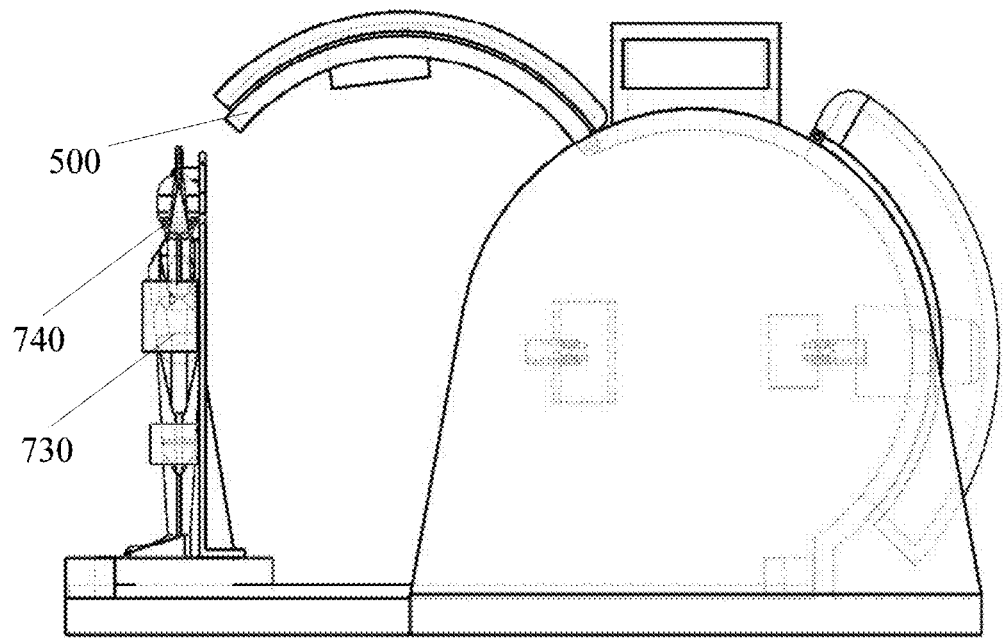
FIG. 4 shows a schematic diagram of a positioning state of a beam irradiation apparatus according to an embodiment of the present application.
Figure 5:
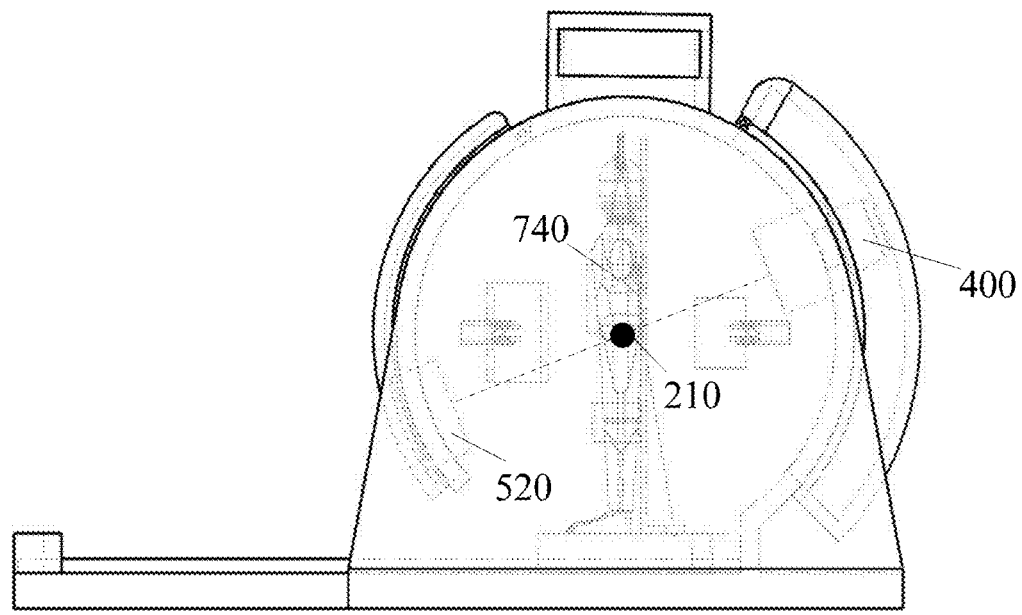
FIG. 5 shows a schematic diagram of a treatment state of a beam irradiation apparatus according to an embodiment of the present application.

FIGS. 4-5 show the state of positioning and radiotherapy of the patient respectively, by using the beam irradiation device of this embodiment. As shown in FIG. 4, when the patient is being positioned, the supporting base 710 of the human body supporting structure 700 abuts against the first stopper 120, and the patient 740 stands or sits on the supporting base 710. Then a body cover 730, such as a thermoplastic film, a vacuum pad, a strap, or polyfoam and accessories alike supplied in advance are used to securely fix the patient on the supporting frame 720. Then the supporting base 710 is controlled to move, and the initial positioning is completed, for example, by adjusting a marking point on the body of the patient to align with a position set by an external positioning device such as an external laser light. Afterwards, the entry door is opened, and the patient is transported by the human body supporting device 700 along the third guide rail 110 to the treatment position, where the supporting base 710 abuts against the second stopper 130. When preparing to adjust the position of the patient, as shown in FIG. 5, the entry door 500 is closed, and the imaging assembly 600 starts to work, which may perform orthogonal and perspective imaging of the patient, or perform CBCT imaging of the patient with the aid of the rotational movement of the supporting base 710, or perform magnetic resonance imaging, to determine a position error of the tumor target area. The positioning error can be corrected through the movement of the supporting base 710, to complete the positioning of the patient. Afterwards, according to a predetermined radiotherapy plan, the human body supporting structure and the beam treatment head 400 may cooperate to achieve coplanar or non-coplanar 3DCRT, IMRT, VMAT, 4π or other radiotherapy techniques. During the treatment process, the imaging assembly 600 can also be used to perform real-time imaging of the target area to monitor the movement of the target area, so that a self-adaptive radiotherapy can be realized.

Figure 6:
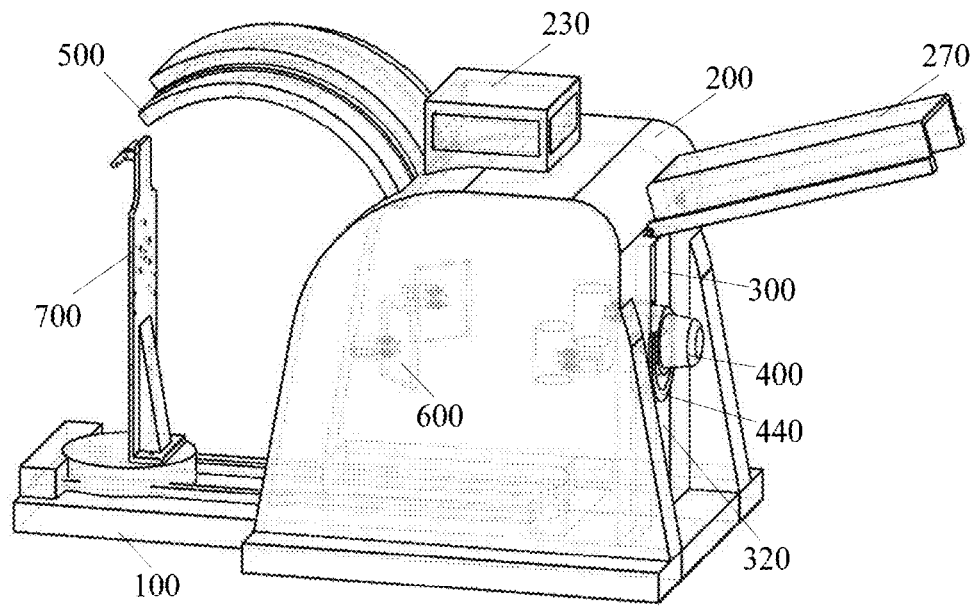
FIG. 6 is a perspective view of a beam irradiation apparatus according to another embodiment of the present application.
Figure 7:
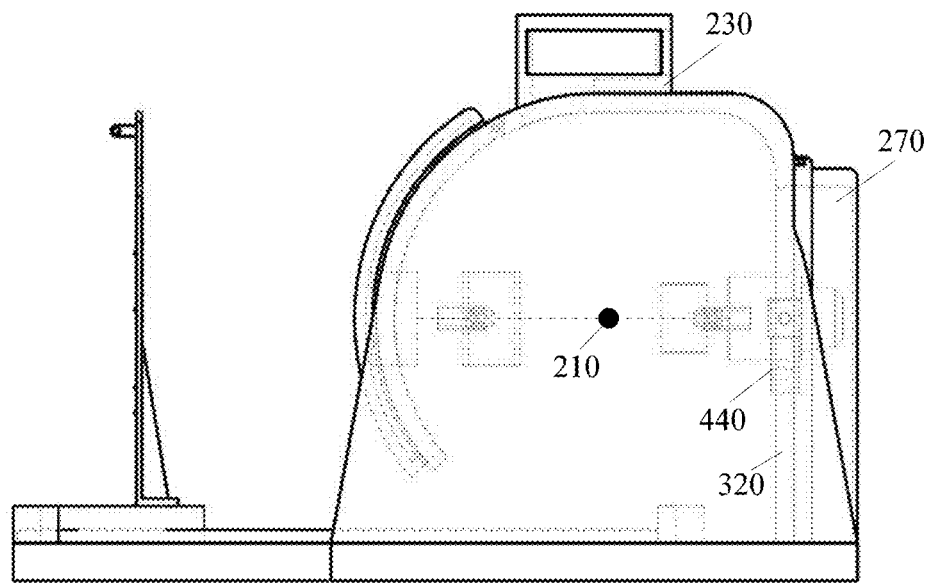
FIG. 7 is a front view of a beam irradiation apparatus according to another embodiment of the present application.

In another exemplary embodiment of the present application, as shown in FIGS. 6-7, the first guide rail 300 supporting the treatment head 400 and guiding it to move may be a linear one, which is vertically installed on the gantry 200. The beam irradiation treatment head 400 can vertically slide up and down along the first guide rail 300 for a certain distance, and can swing at a certain angle, so that the central axis of the beam generated at any position can pass through the treatment center 210. In this embodiment, as shown in FIG. 7, the treatment head 400 comprises a radiation source 410, a collimator 420, a treatment head frame 430, and a sliding frame 440, wherein the radiation source 410 may be an X-ray or electrons or other particles generated by an accelerator, or gamma rays produced by radioactive materials. The collimator 420 is fixedly installed below the radiation source 410, and the radiation source 410 is fixedly installed on the treatment head frame 430. The treatment head frame 430 is rotatably installed on the sliding frame 440, and both sides of the sliding frame 440 are provided with sliding grooves that can slide on the first guide rail 300. Compared with the embodiment shown in FIG. 1, the treatment head of this embodiment is additionally provided with a sliding frame on which the treatment head frame is mounted through the rotating shafts on both sides. The sliding frame are provided with sliding chutes on both sides of the sliding frame, through which the sliding frame is liftably arranged on the first guide rail, so that the sliding frame can drive the radiation source to move up and down, and the radiation source can swing relative to the sliding frame. Further, in this embodiment, the rear shielding plate 270 is generally linear and has a H-shaped cross section, so that it can abut against the side of the gantry 200 without colliding with the treatment head 400 when closed.

Figure 8:
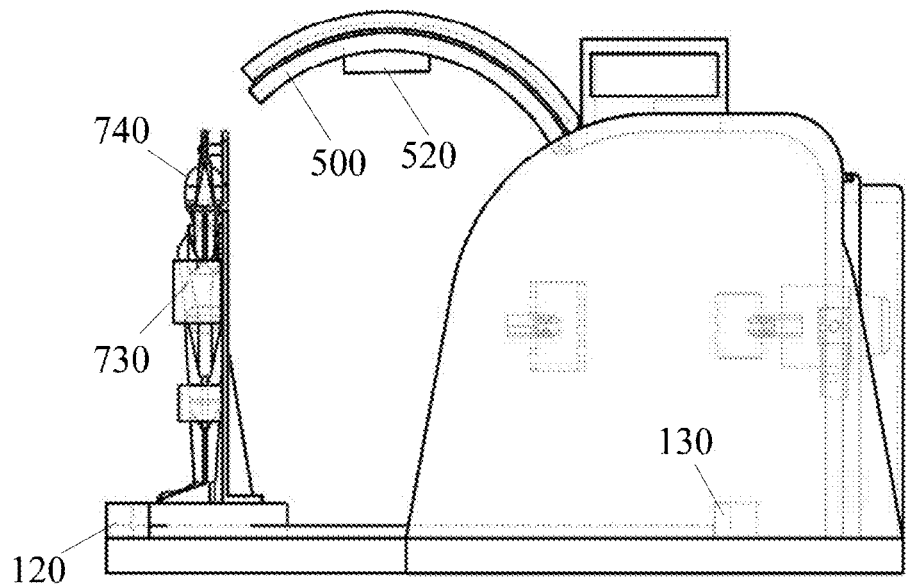
FIG. 8 shows a schematic diagram of a positioning state of a beam irradiation apparatus according to another embodiment of the present application.
Figure 9:
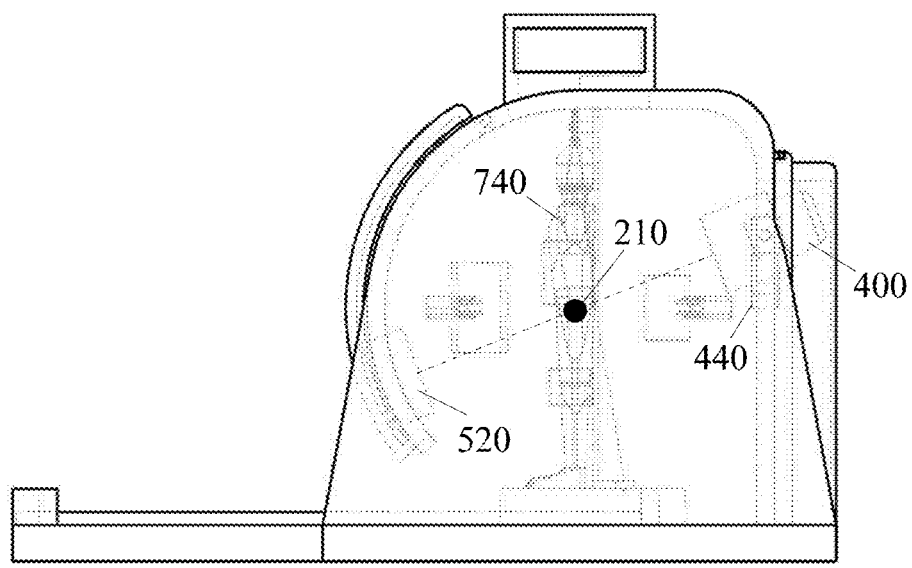
FIG. 9 shows a schematic diagram of a treatment state of a beam irradiation apparatus according to another embodiment of the present application.
Figure 10:
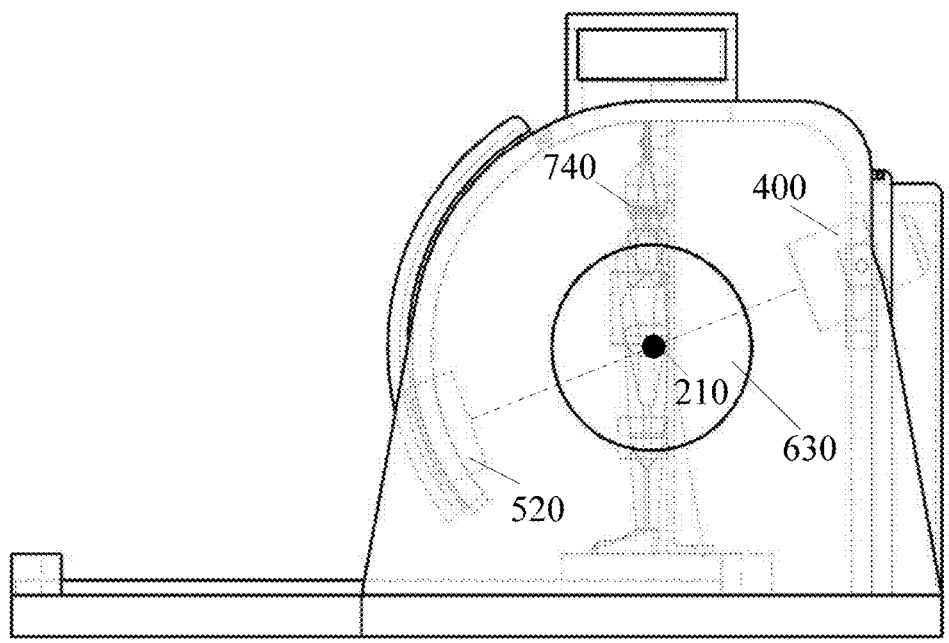
FIG. 10 shows a schematic diagram of a treatment state of a radiotherapy apparatus based on MRI imaging according to another embodiment of the present application.

FIGS. 8-10 show the state of the positioning and radiotherapy of the patient by using the beam irradiation apparatus of this embodiment. As shown in FIG. 8, in this embodiment, the positioning state of the patient can be the same as the embodiment shown in FIG. 4. The positioning error of the patient may be obtained by either the kV-level cone beam imaging assembly or the fan beam imaging assembly 600 (as shown in FIG. 9), or it may be obtained by using the magnetic resonance MRI imaging assembly 630 (as shown in FIG. 10), which will not be repeated here.

In this embodiment, the treatment state of the patient is slightly different from the embodiment shown in FIG. 5. As shown in FIGS. 9-10, during coplanar radiotherapy, the body height of the patient can be adjusted through the supporting base 710 to allow the central axis of the radiation beam of the treatment head aimed with the target area of the patient. Alternatively, it also could be achieved by that the central axis of the radiation beam is controlled to aim at the target area by the lifting movement of the treatment head along the first guide rail 300. When performing non-coplanar radiotherapy, the beam treatment head needs to subject to up and down adjustment first, then swing adjustment, so as to aim at the target area at a non-coplanar angle. Coplanar or non-coplanar 3DCRT, IMRT, VMAT, 4π and other radiotherapy techniques can be implemented using this embodiment, also spiral radiotherapy can be implemented by matching the lifting movement of the treatment head with the rotation movement of the supporting base.

The beam irradiation apparatus according to the disclosed embodiment of the present application can provide coplanar or non-coplanar radiotherapy for patients in a standing or sitting posture. It also has functions such as imaging guidance and positioning correction, and can achieve various high-precision radiotherapy techniques. Further, through the design of self-shielding, the beam is limited within the cabin type radiotherapy apparatus, thereby reducing the protection design requirements of the machine room, and thus reducing the construction cost and manufacturing difficulty of the machine room.

Figure 11:
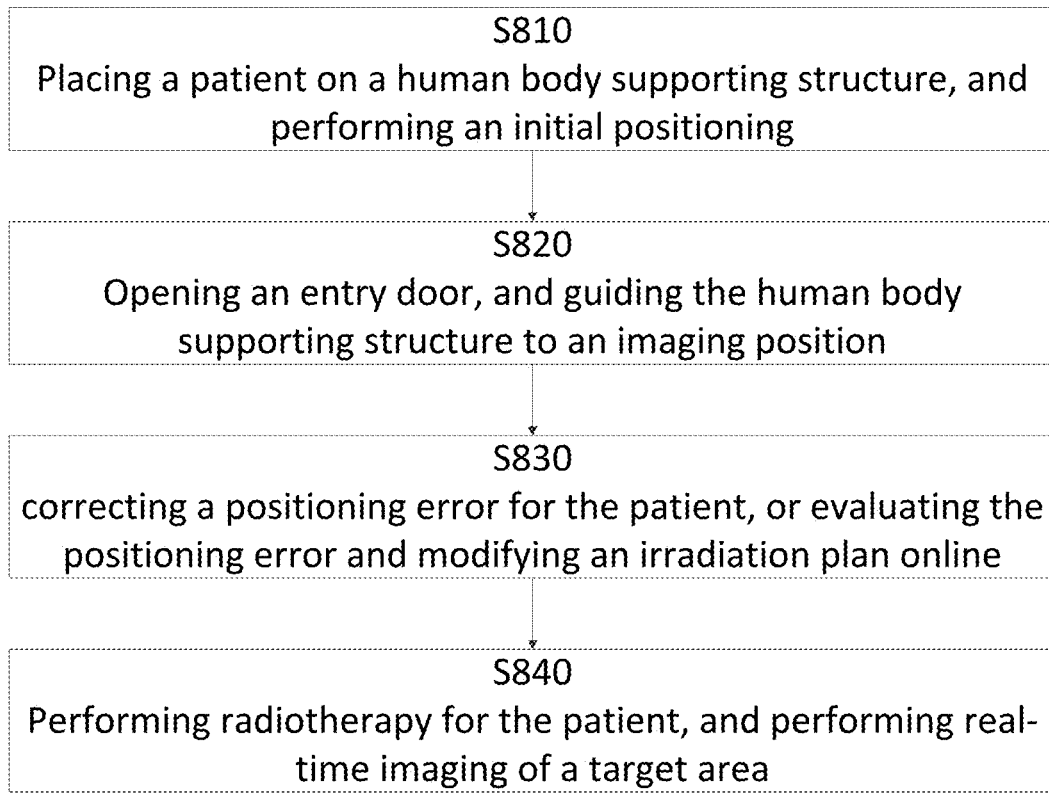
FIG. 11 is a flowchart of a positioning method and a beam irradiation method for radiotherapy according to an embodiment of the present application.

FIG. 11 shows a flow chart of a positioning method and a beam irradiation method for radiotherapy according to an embodiment of the present application. As shown in FIG. 11, the method according to the embodiment of the present application may comprise: step S810: using a positioning body cover to fixedly place a patient in a standing or sitting posture on a human body supporting structure of a beam radiation apparatus, for performing an initial positioning; step S820: opening an entry door of the beam irradiation apparatus, and guiding the human body supporting structure to an imaging position, the imaging position is located in an enclosed space of the beam irradiation apparatus; step S830: closing the entry door, imaging a target area of the patient by using an imaging assembly of the radiotherapy apparatus to obtain a positioning error, and correcting the positioning error; or modifying an irradiation plan based on an evaluation of the positioning error and an anatomical structure change obtained through the imaging; and step S840: performing beam irradiation on the patient according to a treatment plan, wherein during the irradiation process, the imaging assembly performs real-time imaging of the target area, and monitors the position and morphology of the target area to realize controlled or real-time tracking irradiation.

The positioning and beam irradiation process according to the embodiment of the present application can be implemented using the beam irradiation apparatus shown in FIGS. 1-3, or another beam irradiation apparatus shown in FIGS. 6-7.

In step S810, unlike the existing body cover used for lying patient, the present application may use a positioning body cover for patients in a standing or sitting posture. The body cover can be made of a thermoplastic film, vacuum pad, strap or styrofoam. A marking point can be provided on the positioning body cover, and three positioning laser lights orthogonal to each other can be used to help achieve a relative fixation of the patient and the human body supporting structure. The initial positioning can be performed by the movement of the human body supporting structure until the marking point on the positioning body coincides with the marking lines of the three groups of positioning laser lights. If magnetic resonance imaging is used for positioning verification, it is also necessary to install an excitation coil on the human body support structure and aim it at the tumor target area.

In step S820, the entry door can be opened upwardly manually or electrically, and the human body supporting structure is located at the initial position to prevent the entry door from colliding with the supporting frame. After the entry door is opened, the human body supporting structure can be electrically or manually driven to move along a guide rail to the imaging position inside the hollow portion of the beam radiation apparatus. At the imaging position, the base of the human body supporting structure abuts against a stopper to prevent shaking of the human body, thereby facilitates accurate positioning of the patient.

In step S830, the imaging assembly may utilize cone beam imaging, fan beam imaging, or magnetic resonance imaging, to determine a positioning error through the imaging. Afterwards, the operator reviews the positioning error and gives control instructions to correct the positioning error, for example, through the movement of the human body supporting structure. Alternatively, the treatment plan can be modified online to correct the impact of positioning error. Specifically, by evaluating the positioning error and the changes in the anatomical structure of the target area obtained by a cross-sectional image of the human body obtained by the imaging assembly, the irradiation plan can be modified. For example, the beam emitting direction and beam intensity of the treatment head can be adjusted. By correcting the positioning error or modifying the irradiation plan online, the target area of the patient can be positioned at the treatment center, that is, the beam will be aimed at the center of the target tumor, thereby facilitating the implementing of the predetermined irradiation plan.

When one group or two groups of cone beam imaging assemblies are used, the cone beam imaging assembly can be used to collect a multi-angle perspective image of the patient while the human body supporting structure drives the patient to rotate, and to reconstruct a three-dimensional image. When fan beam imaging is used, the human body supporting structure can drive the patient to lift and lower and rotate, and at the same time one or two fan beam imaging assemblies are used to perform axial scan or spiral scan imaging. When magnetic resonance imaging is used, the patient remains fixed, an excitation coil installed on the human body supporting structure emits magnetic signals, and the magnet on the gantry can receive the signals for MRI imaging.

In step 840, in a case the target area of the patient may be shifted due to the patient breathing during the irradiation process, the position and morphology of the target area can be monitored through real-time imaging of the target area by the imaging assembly. When the position and/or morphology exceed a preset threshold, the irradiation beam can be controlled in real time or the shape of the irradiation field can be adjusted to conform to the changed target area.

In one embodiment, if the position of the target area exceeds a limited area due to breathing movement, etc., the treatment head can be controlled to automatically stop beaming by means of gate control circuit, etc., and it will not continue beaming until the position of the target area returns to be within a safe limit. In another embodiment, if the position of the target area exceeds the limited area due to breathing movement, the treatment head does not stop emitting beams, rather adjust the position parameters of the radiation source by moving along a guide rail or change the shape of the leaf collimator to adjust the distribution of beams and so on according to the changes in the position and morphology of the target area.

Imaging monitoring can be performed by using cone beam imaging, fan beam imaging or magnetic resonance imaging. For example, if one group of cone beam imaging assembly is adopted, the position and shape of the target area can be monitored in conjunction with the orthogonal and perspective images obtained by the radiation detector. If two groups of orthogonal cone beam imaging assemblies or fan beam imaging assemblies are used, the position and shape of the target area can be monitored through orthogonal and perspective images of the target area obtained by the two groups of imaging assemblies in real time. If magnetic resonance imaging is used, the position and shape of the target area can be monitored by acquiring tomographic images of the target area in real time.

The radiotherapy process of the present application will be described below with reference to the accompanying drawings. It may be implemented using the treatment device shown in FIGS. 1-3, or another treatment device shown in FIGS. 6-7. Specifically, the radiotherapy process of the present application can be carried out according to the following steps: (1) performing a simulated positioning on the patient to obtain a simulated positioning image of a tumor target area, and preparing a positioning body mask; (2) delineating the target area and the organs at risk according to the simulated positioning image of the patient, and designing a radiotherapy plan; (3) performing an initial positioning on the patient and correcting a positioning error; (4) performing radiotherapy on the patient according to the radiotherapy plan; (5) after completion of the radiotherapy, opening an entry door to return a body supporting device to the initial position, removing the positioning body cover, and guiding the patient away from the human body supporting device.

In step (1), as mentioned above, different from the existing preparation method for making a human body cover for a lying patient, the present application may use a positioning body cover for a patient in standing or sitting posture. Conventional CT can be used to obtain simulated images of the human body in a lying state, and a simulated positioning images of the patient in the standing or sitting posture can be obtained through an image matching algorithm. Alternatively, a vertical CT can be used to obtain the simulated positioning image of the patient in the standing or sitting posture.

In step (2), a radiation plan designer may analyze an area of the target volume and surrounding organs at risk according to the positioning image. Generally, a radiotherapy plan needs to ensure the radiation dose to the target area meets the prescription requirements. It is preferable to make the radiation dose received by organs at risk around the target area within a predetermined range, for example, to minimize the radiation dose received by the organs at risk around the target area.

In step (3), the positioning or positioning correction for a patient can be performed according to the method described above with reference to FIG. 10, so that the target area of a patient coincide with the treatment center of the radiotherapy device after the adjustment of the positioning, the details of which will not be repeated herein.

In step (4), an imaging assembly can be used during radiotherapy to monitor the position of the target area in real time. If the position of the target area exceeds a safe limit due to breathing movement or the like, the treatment head can be controlled to stop beaming automatically until the target area position returns to be within the safe limit. When performing a non-coplanar radiotherapy plan, the treatment head and the human body supporting device can cooperate with each other automatically. When performing spiral tomographic radiotherapy with the radiotherapy device shown in FIGS. 6-7, the treatment head can be stepped up and down while the supporting base of the supporting structure drives the human body to rotate.

In step (5), the beam treatment head may be controlled to terminate or shutter the beam. Then the entry door is opened upward manually or electrically, and the human body supporting structure is moved electrically or manually along the guide rail towards the initial position, until it abuts against the stopper. Afterward, the entry door may be closed, and the positioning body cover of the patient can be disassembled. The patient may be guided to leave the human body supporting structure, thereby finishing the radiotherapy.

The principle of the present application has been described above with reference to specific embodiments. Those skilled in the art will understand that the present application is not limited to the above mentioned embodiments, and various modifications and changes in details and forms can be made without departing from the spirit and scope of the present application. The scope of the present application is defined by the appended claims and their equivalents.

What is claimed is:

1. A cabin type beam irradiation apparatus, comprising:
   a gantry having a hollow frame structure, the hollow portion of which being formed as a treatment cabin;
   a first guide rail fixedly arranged on the gantry;
   a treatment head slidably arranged on the first guide rail; and
   an entry door openably and closably arranged on the gantry.

2. The cabin type beam irradiation apparatus of claim 1, wherein a rotating shaft is installed at one end of the entry door, a mounting hole is formed on an upper part of the gantry, and the rotating shaft and the mounting hole form a revolute pair.

3. The cabin type beam irradiation apparatus of claim 1, wherein a skylight is installed on a top of the gantry, and a window of lead glass for lighting and a ventilation window are arranged around the skylight.

4. The cabin type beam irradiation apparatus of claim 1, further comprising:
   a second guide rail fixedly arranged on the entry door and is arranged opposite to the first guide rail; and
   a radiation detector slidably arranged on the second guide rail.

5. The cabin type beam irradiation apparatus of claim 1, further comprising:
   an imaging assembly fixedly arranged on the hollow frame structure.

6. The cabin type beam irradiation apparatus of claim 5, wherein the imaging assembly comprises one or more groups of cone beam imaging units or fan beam imaging units or magnetic resonance imaging units.

7. The cabin type beam irradiation apparatus of claim 1, further comprising: a shielding plate including a side shielding plate and/or a main shielding plate and/or a rear shielding plate, wherein the side shielding plate is installed on a side of the gantry, the main shielding plate is installed on an outer surface of the entry door, and the rear shielding plate is installed on a side of the gantry right opposite to the main shielding plate.

8. The cabin type beam irradiation apparatus of claim 1, wherein the first guide rail is an arc-shaped guide rail, and the treatment head comprises a radiation source, a collimator, and a treatment head frame, and
   wherein the collimator is fixedly installed below the radiation source, the radiation source is fixedly installed on the treatment head frame, and the treatment head frame is provided with an arc-shaped chute slidable on the first guide rail.

9. The cabin type beam irradiation apparatus of claim 1, wherein the first guide rail is a linear guide rail, and the treatment head comprises a radiation source, a collimator, a treatment head frame and a sliding frame, and
   wherein the collimator is fixedly installed below the radiation source, the radiation source is fixedly installed on the treatment head frame, the treatment head frame is rotatably installed on the sliding frame, and the sliding frame is provided with a chute slidable on the first guide rail.

10. The cabin type beam irradiation apparatus of claim 1, further comprising:
    a base, on which the gantry is fixedly installed;
    a third guide rail arranged on the base and extending into the hollow portion of the gantry; and
    a human body supporting structure slidably arranged on the third guide rail.

11. The cabin type beam irradiation apparatus of claim 10, wherein, the human body supporting structure comprises a supporting base and a supporting frame, and
    wherein the supporting base is slidably arranged on the third guide rail, and the supporting frame is arranged on the supporting base, by which the supporting frame is driven to move in multiple degrees of freedom.

12. The cabin type beam irradiation apparatus of claim 10, further comprising:
    a stopper including a first stopper and a second stopper, wherein the first stopper is installed at one end of the base, for defining an initial position of the human body supporting structure, and the second stopper is installed at another end of the base, for defining a treatment position of the human body supporting structure.

* * * * *